United States Patent [19]

Behrenz et al.

[11] Patent Number: 4,863,909
[45] Date of Patent: Sep. 5, 1989

[54] SYNERGISTIC PESTICIDAL COMPOSITIONS

[75] Inventors: Wolfgang Behrenz, Overath; Manfred Schütte, Pulheim, both of Fed. Rep. of Germany

[73] Assignee: Bayer Aktiengesellschaft, Leverkusen, Fed. Rep. of Germany

[21] Appl. No.: 701,066

[22] Filed: Feb. 13, 1985

Related U.S. Application Data

[63] Continuation of Ser. No. 403,610, Jul. 30, 1982, abandoned.

[30] Foreign Application Priority Data

Aug. 18, 1981 [DE] Fed. Rep. of Germany ....... 3132610

[51] Int. Cl.$^4$ .................... A01N 45/00; A01N 47/10; A01N 37/34
[52] U.S. Cl. .................... 514/136; 514/479; 514/490; 514/521
[58] Field of Search ................ 514/136, 479, 490, 521

[56] References Cited

U.S. PATENT DOCUMENTS

| 2,865,943 | 12/1958 | Lorenz | 424/138 |
| 2,956,073 | 10/1960 | Whetstone et al. | 260/461 |
| 3,111,539 | 11/1963 | Böcker et al. | 260/479 |
| 3,891,759 | 6/1975 | Aries | 424/19 |
| 4,218,469 | 8/1980 | Fuchs et al. | 260/340.5 R |
| 4,341,760 | 7/1982 | Matthewson | 424/45 |
| 4,357,348 | 11/1982 | Kasamatsu et al. | 514/479 |
| 4,415,561 | 11/1983 | Behrenz et al. | 424/DIG. 10 |

FOREIGN PATENT DOCUMENTS

| 7318807 | 6/1973 | Japan | 514/136 |
| 0120607 | 9/1981 | Japan | 514/479 |

Primary Examiner—Douglas W. Robinson
Attorney, Agent, or Firm—Sprung Horn Kramer & Woods

[57] ABSTRACT

New arthropodicidal synergistic mixtures comprising the known active compounds (I) the pyrethroid: α-cyano-3-phenoxy-4-fluoro-benzyl 2,2-dimethyl-3-dichlorovinyl-cyclopropanecarboxylate or α-cyano-3-phenoxybenzyl 2,2-dimethyl-3-dibromovinyl-cyclopropanecarboxylate (decamethrine) and (II) 0,0-dimethyl 0-2,2-dichlorovinyl phosphate (dichlorvos) and (III), if desired, 0-isopropoxyphenyl N-methylcarbamate (propoxur). The novel mixtures are particularly suitable for use in aerosols and oil sprays.

17 Claims, No Drawings

SYNERGISTIC PESTICIDAL COMPOSITIONS

This is a continuation, division, of application Ser. No. 403,610, filed July 30, 1982, now abandoned.

The present invention relates to a new arthropodicidal synergistic combinations of certain pyrethroids and dichlorvos, and, if desired, also propoxur.

"Dichlorvos" is the common name for O,O-dimethyl-O-2,2-dichlorovinyl phosphate and "propoxur" is the common name for O-isopropoxyphenyl N-methylcarbamate.

It is already known that propoxur and dichlorvos have a good action against insects and arachnida. These active compounds have therefore been used for several years with great success for combating pests, in particular for combating domestic pests. However, owing to increasing resistance of such pests, the compounds suffer, in practice, like all insecticides actually used to date, from a certain diminution in activity in the course of time, which diminution can restrict their usefulness in certain instances. As a consequence concentrations and amounts required to be used for combating resistant pests have to be continually increased in order to maintain a satisfactory action, until finally the limit is reached at which their use is no longer practical or possible, particularly for economic reasons and reasons of application technology. The development of resistant insect populations causes particular problems since their resistance is directed not only against a particular insecticide but as a rule includes all active compounds from the same class of active compounds, or even from several classes of active compounds which are similar in action.

The solution to the problem of developing suitable agents for combating resistant pests in the domestic field and hygiene field is therefore of particularly great importance.

The present invention now provides a new arthropodicidal composition containing as active ingredients (I) a pyrethroid of the general formula

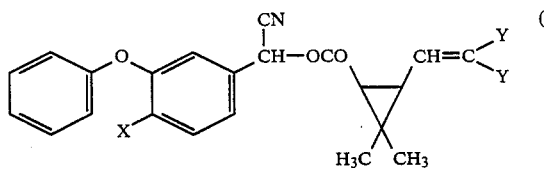

in which
  (a) X represents a fluorine atom and Y represents a chlorine atom ("active compound A") or
  (b) X represents a hydrogen atom and Y represents a bromine atom ("active compound B").
in the form of its individual stereoisomers (enantiomers and diastereomers) or in the form of an isomer mixture thereof, and
(II) dichlorvos of the formula

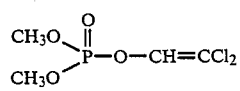

and, if desired,
(III) propoxur of the formula

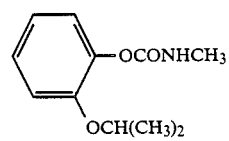

alone or in admixture with a solid or liquid or liquefied gaseous diluent or carrier.

The new compositions of the present invention have a particularly good action against arthropods, in particular against insects and arachnida, and in addition have properties which make them outstandingly suitable for use in the domestic field and hygiene field. In the following "active ingredient (I)" means one of the active compounds A or B in the form of its individual stereoisomers or in the form of an isomer mixture.

The active compounds IB, II and III are active compounds of known commercial products, and the active compound 1 has been disclosed in German Offenlegungsschrift German Published Specification No. DOS 2,709,264 corresponding to U.S. Pat. No. 4,218,469.

Surprisingly, the activity of the composition according to the invention, comprising the active ingredients (I) and (II) or active ingredients (I), (II) and (III), is substantially higher than the sum of the activities of the individual compounds against the pests which are important for the domestic field and hygiene field. Thus, a true synergistic effect, even against strongly resistant domestic and hygiene pests, is present in the compositions according to the present invention.

Arthropodicidal compositions according to the invention are especially formulations which are aerosols and oil sprays, and may be used for combating arthropods, in particular insects and arachnida, very particularly preferably insects, which occur in the domestic and hygiene field.

Preferred pyrethroids of active ingredient (I) are α-cyano-3-phenoxy-4-fluorobenzyl 2,2-dimethyl-3-dichlorovinyl-cis/trans-cyclopropanecarboxylate (preferred as "active compound 1"), and 1R-cis-α-cyano-3-phenoxybenzyl 2,2-dimethyl-3-dibromovinyl-cyclopropanecarboxylate (as "active compound 2").

The proportions of the active compounds can vary within relatively wide ranges in the active compound mixtures or pest-combating agents according to the invention. To achieve best results, the proportions (parts by weight) of the active ingredients (I) to (II) in a two-component combination should be preferably from 1:100 to 1:1, especially from 1:100 to 1:5, and those of active ingredients (I), (II) and (III) in a three-component combination should be from 1:100:100 to 1:1:1, especially from 1:100:100 to 1:10:10. The proportions of the active ingredients (II) and (III) can also vary within the given range. Of course, these proportions need not correspond to integers.

Particularly preferred arthropodicidal compositions according to the present invention are those in which the proportions (parts by weight) of the active ingredients (I) to (II) are about 1:20, about 1:40 or about 1:100, and those of the active ingredients (I), (II) and (III) are about 1:20:20, about 1:30:40, about 1:50:100 or about 1:100:100.

Arthropodicidal compositions according to the present invention which contain all the active ingredients (I), (II) and (III) are particularly preferred.

The arthropodicidal compositions according to the invention for use in the domestic field and hygiene field have an excellent knock-down action and fatal action on the most diverse insect and arachnida pests, in particular insects.

In this respect, the rapid knock-down action is very important, particularly in combating domestic pests, since the user lays great value on a rapid elimination of the annoyance, particularly for reasons of hygiene. The new pest-combating agents are much more effective against pests which are resistant to carbamates, phosphoric (phosphonic) acid esters and pyrethroids, and can therefor be employed in much smaller amounts or concentrations and with better success than pest-combating agents which contain only a single one of active ingredients (I), (II) and (III) All the properties of arthropodicidal compositions must be specifically adapted to the needs of the consumer in the domestic field and hygiene field, and this requires a very specific choice of active compounds (and also of additives).

In addition to a rapid knock-down action, the arthropodicidal compositions according to the invention are distinguished by an enduring residual action on the most diverse substrates.

The abovementioned pests include:
from the order of the Thysanura, for example, Lepisma saccharina;
from the order of the Orthoptera, for example, Blatta orientalis, Periplaneta americana, Leucophaea maderae, Blattella germanica and Acheta domesticus;
from the order of the Dermantera, for example, Forficula auricularia;
from the order of the Isoptera, for example, Reticulitermes spp.;
from the order of the Heteroptera, for example, Cimex lectularius, Rhodnius prolixus and Triatoma spp.;
from the order of the Lepidoptera, for example, Ephestia keuhniella and Galleria mellonella;
from the order of the Coleoptera, for example, Anobium punctatum, Rhizopertha dominica, Bruchidius obtectus, Acanthoscelides obtectus, Hylotrupes bajulus, Oryzaephilus surinamensis, Sitophilus spp., Dermestes spp., Trogoderma spp., Anthrenus spp., Attagenus sppl., Lyctus spp., Ptnius spp., Niptus hololeucus, Gibbium psylloides, Tribolium spp. and Tenebrio molitor;
from the order of the Hymenoptera, for example, Lasius spp., Monomorium pharaonis and Vespa spp.;
from the order of the Diptera, for example, Aedes spp., Anopheles spp., Culex spp., Drosophila melanogaster, Musca spp., Fannia spp., Calliphora erythrocephala, Lucilia spp., Chrysomyia spp., Stomoxys spp. and Tabanus spp.;
from the order of the Siphonaptera, for example, Xenopsylla cheopis and Ceratophyllus spp.;
from the order of the Arachnida, for example, Scorpio maurus and Latrodectus mactans;
from the order of the Acarina, for example, Acarus siro, Argas spp., Ornithodoros spp., Dermanyssus gallinae, Boophilus spp., Rhipicephalus spp., Amblyomma spp., Hyalomma spp. and Ixodes spp.

The arthropodicidal compositions of the invention can be made up as any of the formulatiosn customary in the domestic field and hygiene field. As already mentioned, aerosols (in particular spray cans) and oil sprays are preferred as formulations for the active ingredients.

Aerosol recipes are preferably composed of the active ingredients mentioned, solvents, such as lower alcohols (for example methanol, ethanol, propanol and butanol), ketones (for example acetone and methyl ethyl ketone), paraffin hydrocarbons (for example kerosenes) have boiling ranges of from about 50° to 250° C., chlorinated hydrocarbons (for example methylene chloride or 1,1,1-trichloroethane), aromatic hydrocarbons (for example toluene and xylene), water, and also auxiliaries, such as emulsifiers, such as sorbitan monooleate, oleyl ethoxylate having 3–7 mols of ethylene oxide, fatty alcohol ethoxylate, perfume oils, such as ethereal oils, esters of medium molecular weight fatty acids with lower alcohols, aromatic carbonyl compounds, if appropriate stabilizers, such as sodium benzoate, amphoteric surface-active agents, lower epoxides, triethyl orthoformate, and where required the propellants such as propane, butane, fluorochlorohydrocarbons, dimethyl ether, carbon dioxide, and nitrous oxide, or mixtures of these gases.

In the case of spray cans, the aerosol mixture as a whole is contained in a sufficiently pressure-resistant pack. The material of this pack can be metal (tinplate or aluminum), with or without a separate internal protective lacquer, and glass, with or without a plastic jacketing. Certain plastics (for example polyamide and polypropylene) are also suitable materials.

The aerosol pack has a suitable automatically closing valve of dimensions, shape and materials, such as nozzle openings, nozzle type and sealing materials, best suited to the intended use. The aerosol pack is preferably provided with a suitable protective cap as a safeguard against unintentional operation of the valve.

The oil spray formulations basically differ from the aerosol recipes in using no propellants, since as a rule mechanical pumps are provided for atomization. The solvents and other auxiliaries used are virtually the same as the agents customarily used in aerosol recipes.

The material of the pack for oil spray formulations is much less critical since essentially only tightness and stability to the contents are required. Thus, metals such as iron (predominantly tinplate and/or surface-coated) and aluminum are suitable. Glass and certain plastics, such as polyvinyl chloride, polyethylene and polypropylene, are also suitable.

The choice of the particular solvents and other additives, as well as the type spray cans and the pack depend on the materials present, on the particular fields of use, and on the requirements of the shelf-life of the products, and can be readily determined by one skilled in the art, using his special knowledge and, if appropriate, with the aid of simple generally known methods of investigation.

The compositions contain in general from 0.5 to 90% by weight of the total active ingredients, preferably between 0.5 and 60%.

The compositions are employed in a customary manner appropriate for the use forms.

Owing to their particular properties, the arthropodicidal compositions according to the invention can be employed within a wide range for combating arthropods, in particular insects. Preferred fields of use are public and private hygiene (for example schools, hospitals, foodstuff-processing factories, and households), commercial and private protection of stored products (for example foodstuff stores), as well as use in agriculture and animal husbandry (for example combating stable-flies).

The present invention also provides a method of combating arthropods (especially insects and arachnids) which comprises applying to the arthropods, or to a habitat thereof, a compound of the present invention.

The examples which follow illustrate formulations of arthropodicidal compositions according to the present invention.

FORMULATION EXAMPLES

EXAMPLE 1

| Spray formulation | Parts by weight |
| --- | --- |
| Active compound I | 0.025 |
| Active compound III | 0.5 |
| Methylene chloride | 25.0 |
| Deodorized kerosene/mixture of saturated aliphatic hydrocarbons (for example, isododecane) | 12.37 |
| Perfume oil | 0.03 |
| Stabilizer (butylene oxide, triethyl orthoformate) | 0.1 |
| Propellant: propane/butane (15:85) | 61.975 |

EXAMPLE 2

| Spray formulation | Parts by weight |
| --- | --- |
| Active compound II | 0.01 |
| Active compound III | 1.0 |
| Methylene chloride | 25.0 |
| Deodorized kerosene | 12.37 |
| Perfume oil | 0.003 |
| Stabilizer (as in Example (1)) | 0.1 |
| Propellant: propane/butane (15:85) | 61.517 |

EXAMPLE 3

| Spray formulation | Parts by weight |
| --- | --- |
| Active compound IA | 0.025 |
| Active compound II | 1.0 |
| Active compound III | 1.0 |
| Methylene chloride | 25.0 |
| Deodorized kerosene | 12.37 |
| Perfume oil | 0.03 |
| Stabilizer (as in Example (1)) | 0.1 |
| Propellant: propane/butane (15:85) | 60.475 |

EXAMPLE 4

| Spray formulation | Parts by weight |
| --- | --- |
| Active compound IB | 0.03 |
| Active compound II | 1.0 |
| Active compound III | 1.0 |
| Methylene chloride | 25.0 |
| Deodorized kerosene | 12.37 |
| Perfume oil | 0.03 |
| Stabilizer (as in Example (1)) | 0.1 |
| Propellant: propane/butane (15:85) | 60.47 |

EXAMPLE 5

| Oil spray formulation | Parts by weight |
| --- | --- |
| Active compound IA | 0.01 |
| Active compound II | 0.5 |
| Xylene | 2.0 |
| Deodorized kerosene | 97.49 |

EXAMPLE 6

| Oil spray formulation | Parts by weight |
| --- | --- |
| Active compound IB | 0.005 |
| Active compound II | 0.5 |
| Xylene | 1.0 |
| Deodorized kerosene | 98.495 |

EXAMPLE 7

| Oil spray formulation | Parts by weight |
| --- | --- |
| Active compound IA | 0.02 |
| Active compound II | 0.5 |
| Active compound III | 1.0 |
| Xylene | 2.0 |
| Isopropanol | 10.0 |
| Deodorized kerosene | 86.48 |

EXAMPLE 8

| Oil spray formulation | Parts by weight |
| --- | --- |
| Active compound IB | 0.01 |
| Active compound II | 1.0 |
| Active compound III | 0.5 |
| Xylene | 2.0 |
| Isopropanol | 10.0 |
| Deodorized kerosene | 86.49 |

The arthropodicidal activity of the active compound combinations according to the present invention is illustrated by the following biotest example.

BIOTEST EXAMPLE

EXAMPLE 9

Spray cans or oil sprays, which contained either only "active compound 1A" or "active compound IB" or "active compound II" or "active compound III", as well as spray cans or oil sprays which contains the arthropodicidal compositions of the invention were sprayed in rooms of 30 m$^3$ capacity. 3 wire cages, each containing 20 Musca domestica (♂ ♂, strain Hans) which were very resistant to carbamates, phosphoric (phosphonic) acid esters and pyrethroids, were suspended beforehand in the rooms. After the application (by spraying) of 17 g of formulations per room in each case, the rooms were closed, and the action on the flies was monitored continuously through a window for up to one hour. The number of minutes required for a 50% knock-down effect on the test animals was determined (gives: K.D. 50 values).

The table which follows contains the values determined:

TABLE

Musca domestica (strain Hans, male, multi-resistant)

| Active compounds | % (by weight) of active compounds in the formulation | Knock-down effect in minutes after application KD 50 |
| --- | --- | --- |
| IA | 0.025–0.1 | none |

TABLE-continued

| Musca domestica (strain Hans, male, multi-resistant) | | |
|---|---|---|
| Active compounds | % (by weight) of active compounds in the formulation | Knock-down effect in minutes after application KD 50 |
| IB | 0.01–0.08 | none |
| II | 0.5–1.0 | none |
| III | 0.5–2.0 | none |
| IA + II | 0.025 + 0.5 | 30 |
| IA + II | 0.05 + 0.5 | 22 |
| IA + II | 0.025 + 1.0 | 17 |
| IB + II | 0.01 + 0.5 | 28 |
| IB + II | 0.03 + 0.5 | 22 |
| IB + II | 0.01 + 1.0 | 16 |
| IB + II | 0.03 + 1.0 | 13 |
| IA + II + III | 0.025 + 1.0 + 1.0 | 13 |
| IB + II + III | 0.03 + 1.0 + 1.0 | 11 |

"None" means that a KD 50 was not reached in the course of 1 hour.

It will be appreciated that the instant specification and examples are set forth by way of illustration and not limitation, and that various modifications and changes may be made without departing from the spirit and scope of the present invention.

We claim:

1. An arthropodicidal composition containing as active ingredients
   (I) a pyrethroid of the formula

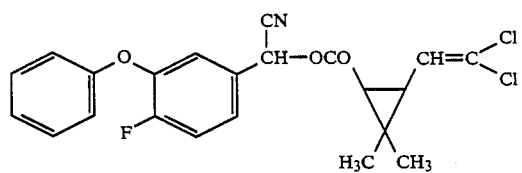

and

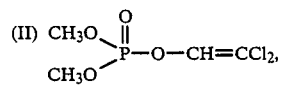

the weight ratio of I:II being from about 1:10 to 1:40.

2. A composition according to claim 1, containing as an additional ingredient

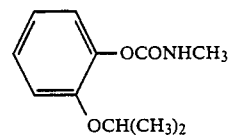

wherein the ratio of I:II: additional ingredient is about 1:40:40.

3. An arthropodicidal composition containing as active ingredients
   (I) a pyrethroid of the formula

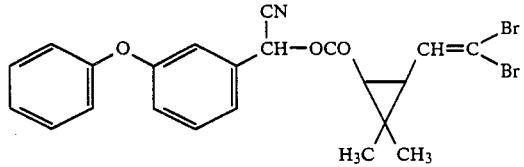

and

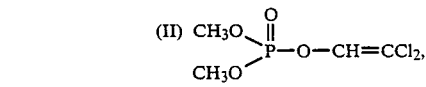

the weight ratio of I:II being from about 1:16 to 1:100.

4. A composition according to claim 3, containing as an additional ingredient

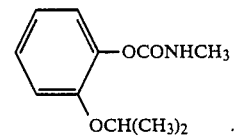

wherein the ratio of I:II:additional ingredient is about 1:33:33.

5. A method of combating arthropods which comprises applying to the arthropods, or to a habitat thereof, an arthropodicidally effective amount of a composition according to claim 1.

6. A method of combating arthropods which comprises applying to the arthropods, or to a habitat thereof, an arthropodicidally effective amount of a composition according to claim 2.

7. A method of combating arthropods which comprises applying to the arthropods, or to a habitat thereof, an arthropodicidally effective amount of a composition according to claim 3.

8. A method of combating arthropods which comprises applying to the arthropods, or to a habitat thereof, an arthropodicidally effective amount of a composition according to claim 4.

9. An arthropodicidal composition comprising
   (I) a pyrethroid of the formula

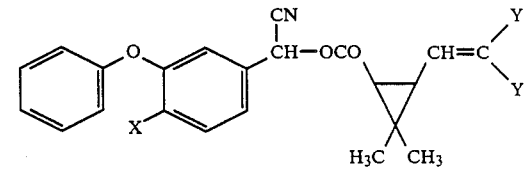

in which (a) X is fluorine and Y is chlorine, or (b) X is hydrogen and Y is bromine, (II) dichlorvos, and (III) propoxur, the weight ratio of I:II:III ranging from about 1:5:10 to 1:50:50.

10. An arthropodicidal composition according to claim 9, wherein the weight ratio of I:II:III is from about 1:50:50 to 1:10:10.

11. An arthropodicidal composition according to claim 9, wherein the weight ratio of I:II:III is about 1:20:20.

12. An arthropodicidal composition according to claim 9, wherein the weight ratio of I:II:III is about 1:30:40.

13. An arthropodicidal composition according to claim 9, wherein the weight ratio of I:II:III is about 1:50:50.

14. An arthropodicidal composition according to claim 9, where I is

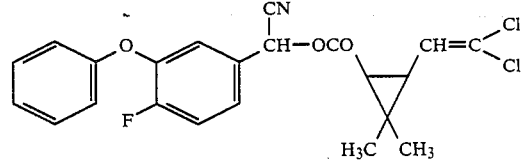

15. An arthropodicidal composition according to claim 9, wherein I is

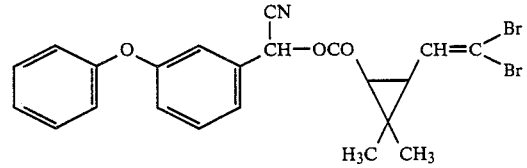

16. An arthropodicidal composition according to claim 9, in which (I) is α-cyano-3-phenoxy 4-fluorobenzyl 2,2-dimethyl-3-dichlorovinyl-cis/trans-cyclopropanecarboxylate or IR-cis-α-cyano-3-phenoxybenzyl-2,2-dimethyl-3-dibromovinyl-cyclopropanecarboxylate.

17. A method of combating Musca domestica comprising applying thereto, or to a habitat thereof, an amount effective therefor of a composition according to claim 9.

* * * * *